United States Patent [19]

Thie et al.

[11] Patent Number: 4,922,920
[45] Date of Patent: May 8, 1990

[54] PROCESS AND APPARATUS FOR PROCESSING SIGNALS FROM A PHYSIOLOGICALLY PRODUCED ELECTRIC FIELD

[75] Inventors: Werner Thie, Winterthur; Johann J. Schmid, Buchs, both of Switzerland

[73] Assignee: Willi Studer AB, Switzerland

[21] Appl. No.: 145,877

[22] Filed: Jan. 20, 1988

[30] Foreign Application Priority Data

Jan. 22, 1987 [CH] Switzerland ............... 00224/87

[51] Int. Cl.⁵ .................................. A61B 5/04
[52] U.S. Cl. ........................ 128/699; 364/413.06
[58] Field of Search .......... 128/699, 653, 695, 696, 128/700, 704, 706; 364/413.05, 413.06

[56] References Cited

U.S. PATENT DOCUMENTS

| | | | |
|---|---|---|---|
| 4,085,407 | 4/1978 | Stratbucker et al. | 346/33 ME |
| 4,292,977 | 10/1981 | Krause et al. | 128/712 |
| 4,547,892 | 10/1985 | Richey et al. | 128/653 |
| 4,587,976 | 5/1986 | Schmid et al. | 128/699 |
| 4,697,597 | 10/1987 | Sanz et al. | 128/699 |
| 4,700,712 | 10/1987 | Schmid | 128/699 |

FOREIGN PATENT DOCUMENTS

| | | | |
|---|---|---|---|
| 0150352 | 8/1985 | European Pat. Off. | 128/699 |
| 0223049 | 5/1987 | European Pat. Off. | 128/699 |
| 2719803 | 2/1978 | Fed. Rep. of Germany | 128/696 |

OTHER PUBLICATIONS

Communications of the ACM, vol. 5, No. 2, Feb. 1962, (New York, US), G. E. Forsythe et al: "Vectorcardiographic Diagnosis with the Aid of ALGOL", pp. 118–122.
Electronics and Communications in Japan, vol. 57-c, No. 3, 1974, A. Nishiyama et al.: "An Automatic Heart-Disease Diagnosis System Using an MOS-IC'ed Learning Machine", pp. 86–92.

Primary Examiner—Francis Jaworski
Assistant Examiner—George Manuel
Attorney, Agent, or Firm—Roylance, Abrams, Berdo & Goodman

[57] ABSTRACT

In the invention method and apparatus where electric signals are tapped as potentials in a physiologically produced electric field, a vector is determined which represents the instantaneous state of an electric dipole. In order to be able to substantially determine and interpret the movement of a vector, the time patten of the vector is also determined. This includes the determination of differential vectors, surfaces covered by the vector, loops forming the vector and projections of said loops in a plane.

16 Claims, 4 Drawing Sheets

PROCESS AND APPARATUS FOR PROCESSING SIGNALS FROM A PHYSIOLOGICALLY PRODUCED ELECTRIC FIELD

FIELD OF THE INVENTION

This invention relates to a process and apparatus for processing electric signals tapped or sampled as potentials in a physiologically produced electric field.

DISCUSSION OF THE PRIOR ART

U.S. Pat. No. 4,569,357 discloses a process and apparatus which makes it possible to tap and process these electric signals in such a way that from them can be obtained a spatial representation of a vector which represents the electric field as produced by the heart of a living organism. The maximum value of this vector and the time at which it occurs, as well as the direction of the vector at this time, are determined.

The disadvantage of this known process and apparatus is that the behavior of said vector within a period and within several periods can be only imprecisely determined. Vital information on the activity of the heart is lost, but could be obtained through a more precise and complete determination of the behavior of the vector.

The present invention solves the problem of providing a process and an apparatus making it possible to avoid such disadvantages and enables the movement of the vector in space to be substantially determined and interpreted.

FEATURES AND ADVANTAGES OF THE INVENTION

The advantages obtained by the invention include that the time pattern of the vector is determined in such a way that further quantities or numerical values can be derived therefrom. The comparison of such quantities from successive periods and the comparison of such quantities with corresponding quantities obtained from other fields of the same type make it possible to better determine the state of the heart of a particular patient. As a result of the invention's proposed qualitative, numerical determination of vector loops, it is possible to compare individual vector loops more objectively with one another. This is carried out by obtaining numerical values from each vector loop, which can be adequately compared with one another. Such numerical values include lengths of differential vectors, surfaces of projections of vector loops on planes, absolute values of vectors, as well as the time function of said values, vector time surfaces, vector value time surfaces, etc. A processor system makes it possible to link these numerical values, which in turn gives further information.

BRIEF DESCRIPTION OF THE DRAWING

The inventin is described in greater detail hereinafter and with reference to the drawings which also form a part of this disclosure, and wherein:

FIG. 3 shows vector loops and their projections on a plane;

DETAILED DESCRIPTION OF THE PREFERRED EMBODIMENTS

Figure 1:
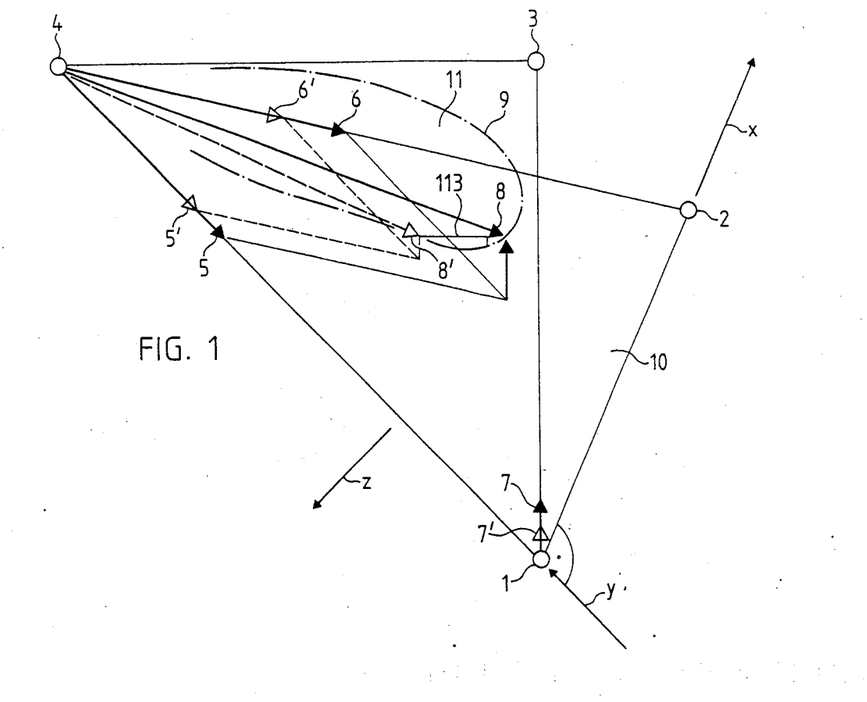
FIG. 1 is a diagrammatic representation of several vectors in space.

FIG. 1 shows four positions 1, 2, 3 and 4 for electrodes in a physiologically produced field as produced by an organism, not shown, such as, for example, a human being. Electric potentials are determined at positions 1 to 4. Potential differences between in each case two positions are represented by partial vectors 5, 5', 6, 6' and 7, 7'. Partial vectors 5, 6 and 7 are determined at a specific first time and partial vectors 5', 6' and 7' at a specific second time. By vector addition vector 8 at the first time and vector 8' at the second time are obtained. Loop 9 shown in a dot-dash line manner indicates the geometrical locus assumed by the point of vector 8, 8' at successive times in a period. Positions 1, 2 and 4 define a plane 10, which is substantially parallel to a surface 11 defined by loop 9. Surface 11 is generally not necessarily planar. Axes x, y and z for an orthogonal coordinate system are shown. The z-axis is at right angles to a plane covered by the x and y-axes.

This manner of determining vector 8 is also described in U.S. Pat. No. 4,569,357 referred to above.

Figure 2:
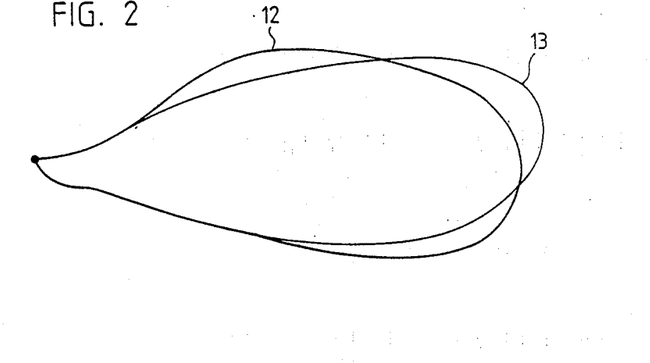
FIG. 2 shows loops which describe the points or tips of vectors.

FIG. 2 shows loops 12 and 13 obtained at different times from the same field of one organism or from different individual organisms.

Figure 3:
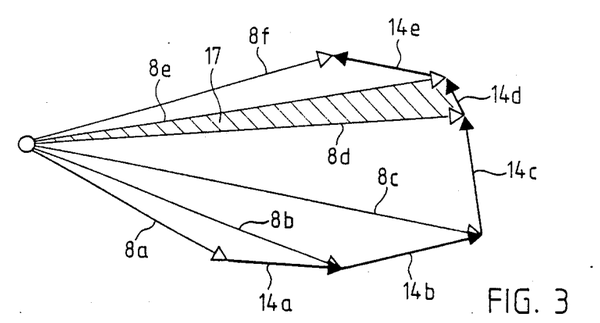
FIG. 3 shows several vectors with their differential vectors.

FIG. 3 shows vectors 8a, 8b, 8c, 8d, 8e, and 8f determined e.g. after identical time intervals in a period. A period is understood to be a time interval in which the same physical process takes place constantly, for example, a heart beat interval. Differential vectors 14a, 14b, 14c, 14d and 14e connect in each case to successive vectors 8a, 8b, etc. Differential vectors are quantities derived from vectors and are also a measure of the speed with which the vector 8 changes in said time intervals. A vector time surface 17 is also indicated between vectors 8d and 8e and indicates which surface the vector covers in a unit of time.

Figure 4:
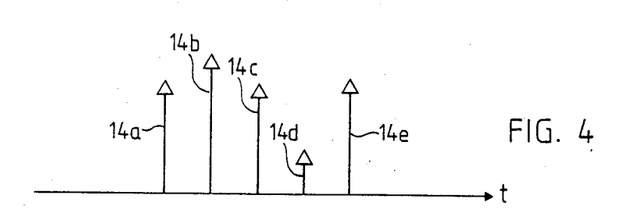
FIG. 4 shows absolute values of the differential vectors according to FIG. 3.

FIG. 4 shows as further quantities the absolute values of the differential vectors 14a to 14e as a function of time. The represented values may be determined within one period.

Figure 5:
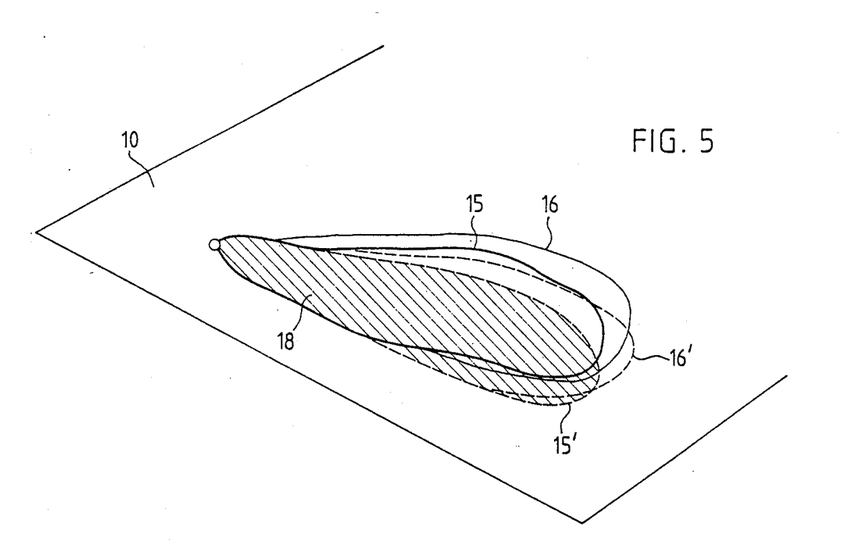

FIG. 5 shows two loops 15, 16 giving the time pattern of vector 8 in different periods, as well as the projections 15', 16' thereof in plane 10 according to FIG. 1. The surface within projection 15' of loop 15 is designated 18 and is covered by the projected vector in one period.

Figure 6:
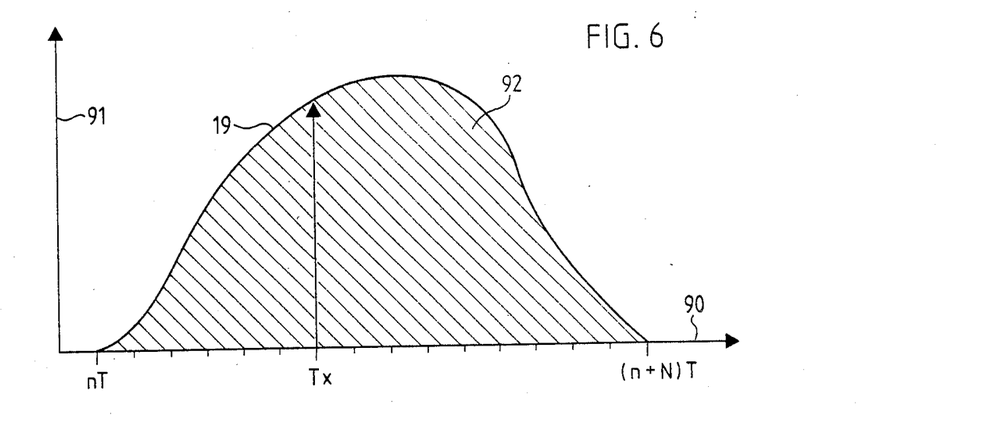
FIG. 6 shows a function of the vectors.

FIG. 6 shows an example of a function 19 of a vector 8, 8', such as is known from FIG. 1. If, for example, starting from position 4, vector 8, 8' passes through the loop 9 in one period, then the absolute values of vector 8, 8' follow the function 19. This means that the horizontal axis is a time axis and that the vertical axis 91 carries values of the vector. Changes to the absolute values of the vector over time can be determined from this function. The surface 92 under the function 29 can also be considered as an integral of the absolute values of the vector over a period.

Figure 7:
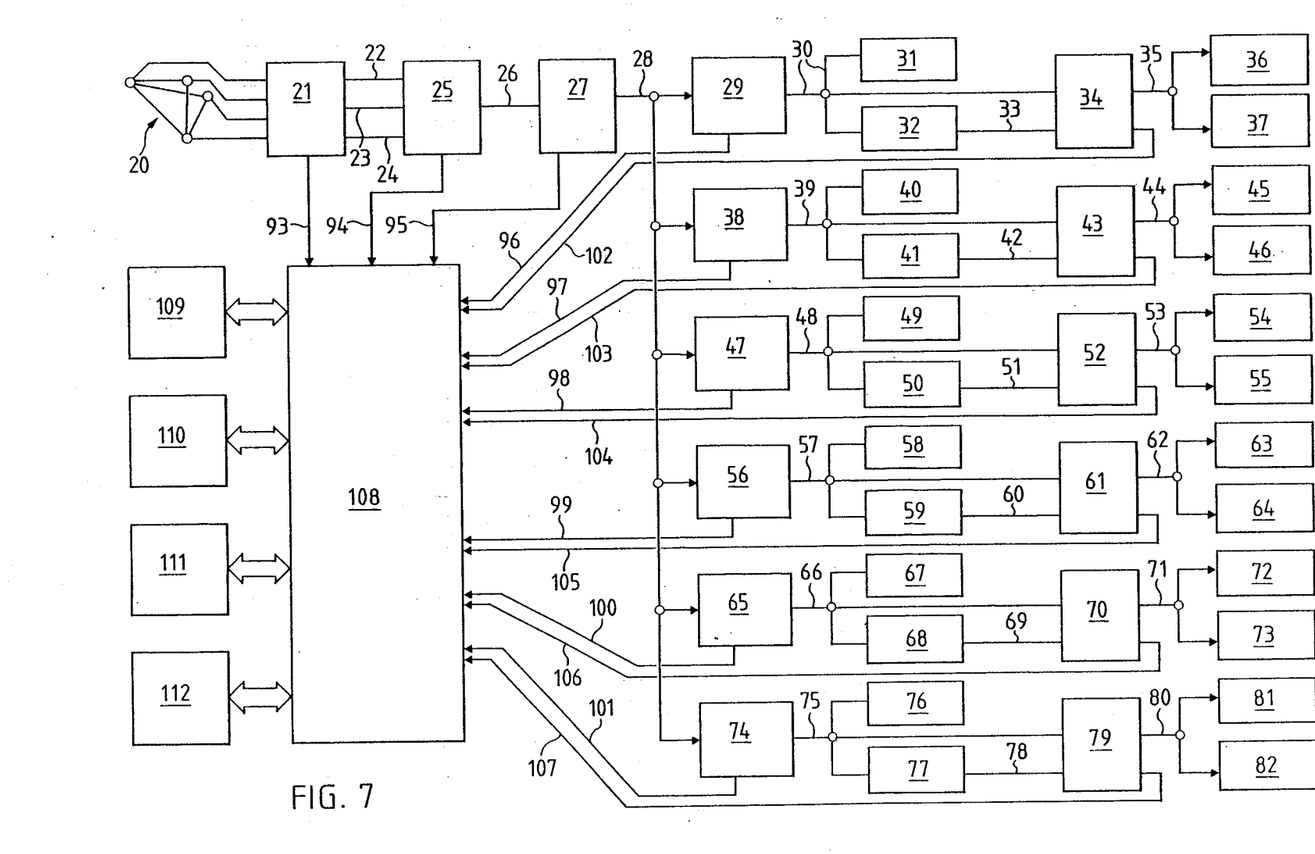
FIG. 7 is a diagrammatic representation of the apparatus.

FIG. 7 is a diagrammatic representation of the invention apparatus, which comprises an arrangement 20 of electrodes positioned in accordance with FIG. 1 and provided with lines. In a known manner, the electrodes tap or sample potentials in a physiologically produced field. These electrodes are connected to a subtracting circuit 21, which will be explained in greater detail relative to FIG. 8. Subtracting circuit 21 forms a means for forming potential diferences and partial vectors. Lines 22, 23 and 24 connect it with a circuit 25 for adding the partial vectors so as to form a vector, the partial vectors being supplied across lines 22, 23 and 24 from the subtracting circuit 21. Such circuits 21 and 25 can be realized by correspondingly programmed microprocessors. A line 26 or a bus connects circuit 25 to a memory circuit 27, which comprises a memory and which makes it possible to store the values of a plurality of stored vectors, so that they are available for further processing operations. It is also possible to see the vectors with their coordinates in the coordinate sysem accordig to FIG. 1 and the time at twhich scanning takes place of the starting values, i.e. the potentials, as described below.

A line 28 or a bus connects the memory circuit 27 to a unit 29 for forming differential vectors. This unit 29 essentially comprises a memory and a computer. It is in a position to calculate the differential vector 113 (FIG. 1) from the modulus and direction of two vectors or from the coordinates of the points of the vectors in accordance with the known rules of vector addition and to give the coordinates thereof in the coordinate system with axes x, y and z. For this purpose the computer of unit 29 is programmed in accordance with these known rules. The calculated values for the differential vector are supplied by means of lines 30 to a display unit 31 and a memory unit 32. The values for the modulus and the position of the differential vector in a coordinate system are displayed in display unit 31. This can take place by outputting the particular numerical values via a printer and/or by graphical representation of the differential vector or all the differential vectors of a period on a screen. Memory unit 32 comprises a RAM and/or a further memory, such as, for example, a tape or disk storage device. From memory unit 32 stored values are supplied via a line 33 and for forming differential vectors unit 28 supplies actual values via line 30 to an evaluation unit 34, which e.g. comprises a computer and a memory. It can determine differences between the values of differential vectors determined at successive times of a period. It can compare actual values with stored values for the same subject or with stored values of another subject of the same type and calculate the variation. The values determined in evaluation unit 34 are supplied by means of a line 35 to a display unit 36 and a memory unit 37, which correspond to units 31 and 32. Unit 29 can also be programmed for calculating the vector time surface 17 (FIG. 3) from the vectors and differential vectors. For example, and the vector time surface 17 can be determined by calculating the surface of a triangle in per se known manner, the triangle being bounded by two vectors 8d, 8e and the differential vector 14d.

The representation and formation of the differential vectors from heart-related vectors makes it easier to detect and bring about a better reciprocal separation of electrophysiological processes, such as the depolarization and repolarization of a dipole (which electrically represents the heart). As is known, a heart beat can be separated into a QRS-wave, a P-wave and a T-wave (see FIG. 8 of U.S. Pat. No. 4,569,357). P- and T-waves are much samller than QRS-waves, which means that the potentials and potential differences are much greater for QRS-waves than for P- and T-waves. For this reason difference vectors which are established or calculated at predetermined times or after predetermined time intervals, will be of a quite different magnitude for QRS-waves than for P- and T-waves. These difference vectors are therefore usable for detecting such QRS-waves and P- and T-waves, as is done in the present invention.

Line 28 is also connected to a unit 38 for representing a vector loop. Unit 38 stores the coordinates of the points of vectors 8 according to FIG. 1 in space for each period and therefore comprises a memory. It can also be supplemented by a computer to which is made available a programme for coordinate transformation. Thus, the vector 8, 8' can be calculated in further coordinate systems and stored in the memory. This means that the coordinates for the vectors of one period can be simultaneously supplied to a display unit and it is possible there to consider the loop 9 e.g. from different directions or in different projections. Thus, by means of lines 39, unit 38 is connected to a display unit 40 and a memory unit 41 making it possible on the one hand to represent such vector loops graphically or by giving values and on the other hand to store the same. A line 42 is provided for connecting memory unit 41 to an evaluation unit 43, which is also connected to unit 38 across lines 39. Evaluation unit 43 comprises a computer and a memory and makes it possible to compare an actual vector loop with a stored, old vector loop. This makes it possible to determine characteristic variations of the contours of the vector loops. These variations can be determined by comparing old and actual values or different old values from the memory for certain selected time intervals. Such variations give information on the performance of electrophysical processes in the organism. Evaluation unit 43 is also connected to a display unit 45 and a memory unit 46 via lines 44.

Line 28 is also connected to a unit 47 for determining the surface of the projection of a vector loop in one plane. Unit 47 comprises a computer and a memory and is connected via lines 48 to a display unit 49 and a memory unit 50. Such a surface to be determined is shown at 18 in FIG. 5 and can therefore be determined in known manner exclusively by using the x and y-coordinates of a vector 8. For this purpose, several vectors 8 are determined at different times during a period and then also the differential vectors 14 for said vectors 8 are determined. The vector time surface can be calculated from in each case two vectors and the associated differential vector. The loop surface 18 is then obtained by the addition of all the vector time surfaces. If several vectors 8 are determined in a period, then the surface 18 with a correspondingly greater accuracy is obtained therefrom. Display unit 49 shows the shape and/or content of surface 18. Memory unit 50 stores the values regarding the shape and/or content of surface 18. A line 51 connects memory unit 50 to an evaluation unit 52. which compares previously measured and stored surfaces with the actual surface. The comparison of the value or size of these surfaces makes it possible to draw conclusions concerning the working of the organism of the living being. Lines 53 connect said evaluation unit 52 to a display unit 54 and a memory unit 55. which display or store surface differences.

Line 28 is also connected to a unit 56 for determining the absolute values of vectors 8, 8'. Unit 56 comprises a computer and a memory and is connected across lines 57 to a display unit 58 and a memory unit 59. Unit 56 calculates the absolute values of vector 8, 8' at different successive times during a period and namely in per se known manner from the squares of the individual partial vectors x, y and z. For example, the absolute values of vector 8 at time Tx is:

$$|v| = |\sqrt{x^2(Tx) + y^2(Tx) + Z^2(Tx)}|$$

These values are also stored in memory unit 59. A line 60 connects memory unit 59 to an evaluation unit 61, which compares stored values with actual values. This makes it possible to determine changes in the electrolyte or in the tissues of the living organism, which are significant for the line of electrical signals. Evaluation unit 61 is connected via lines 62 to a display unit 63 and a memory unit 64.

Line 28 is also connected to a unit 65 for determining the vector modulus time surface 92 (FIG. 6). The vector modulus time surface 92 is bounded in FIG. 3 by the modulus function 19 and the time axis 90. It is assumed that vector 8, 8' requires a period designated $(n+N)T - nT$ for passing through its loop 9 and then the vector modulus time surface is calculated according to the following formula:

$$F = \sum_{i=n}^{n+N} [|\sqrt{X^2(iT) + y^2(iT) + z^2(iT)}| \cdot ((i)T - (i-1)T)]$$

Unit 65 comprises a computer and a memory. It calculates the aforementioned surface according to the formula and gives the results via lines 66 to a display unit 67 and a memory unit 68. This surface 92 gives information on the energy conversion of the electrophysiological processes. A line 69 connects memory unit 68 to an evaluation unit 70 in which stored values are compared with the actual values of the surface. This makes it possible to determine divergences between the just measured version and previously measured values or average values. Lines 71 connect the evaluation unit 70 to a display unit 72 and a memory unit 73.

Line 28 is also connected to a unit 74 for determining the vector at specific times. Unit 74 also comprises a computer and a memory and is connected via lines 75 to a display unit 76 and a memory unit 77. The latter display and store the modulus and direction of the vector at different times. By means of a line 78, memory unit 77 is connected to an evaluation unit 79, which compares old values with new and actual values. The resulting divergences are supplied across lines 80 to a display unit 81 and a memory unit 82.

Circuits 21, 25 and 27, units 29, 38, 47, 56, 65, 74 and evaluation units 34, 43, 52, 61, 70 and 79 are connected via lines 93 to 107 to a processor system 108, which is provided with a display unit 109, an additional memory unit 110 and a documenting unit 111. An input unit 112 for the complete apparatus is connected to the processor system 108 and e.g. comprises a keyboard, which can be supplemented by a screen. The processor system 108 can be a commercially available microprocessor system (e.g. of series 68000). Display unit 109 is also constituted by a known screen and a printer serves as the documenting unit 111. Into the processor system 108 can be fed standard or limit values for all quantities available over lines 93 to 107 preceding the operation of the apparatus. Processor system 108 can then output these quantities, together with said predetermined values to display unit 109 and documenting unit 111, which can together represent the calculated quantities and the predetermined values. Processor system 108 can also be programmed in such a way that it can process and output several quantities supplied to it and values regarding further informations.

As several of the units 29, 38, 47, 56, 65 and 74 have a memory, a computer or both, it is conceivable to provide only one computer and only one memory. Another per se known programme control in this case ensures that the desired computer programmes are performed. Moreover several or even all the display units can be combined into a single display unit. This also applies regarding the memroy unit and lines, which can e.g. be replaced by a bus.

Figure 8:
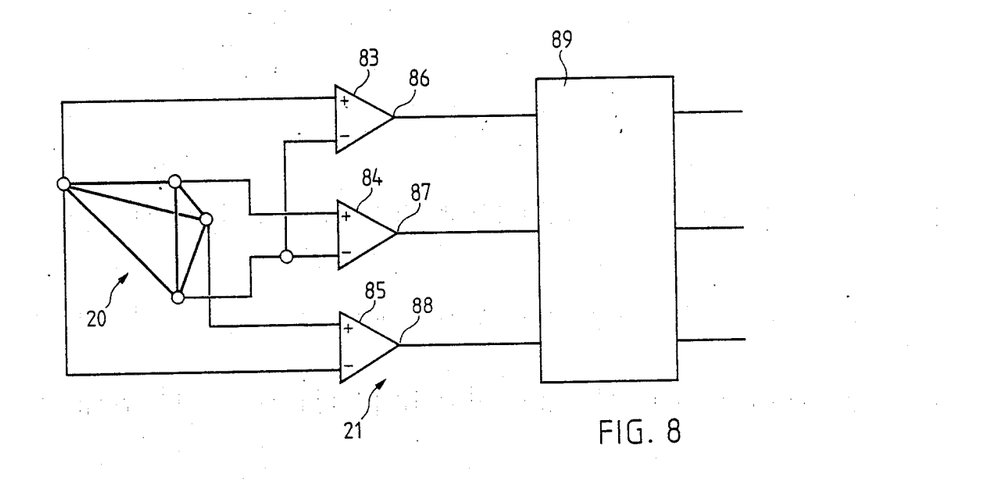
FIG. 8 shows part of the apparatus of FIG. 7.

FIG. 8 shows the arrangement 20 with a subtracting circuit 21 connected thereto and which has three differential amplifiers 83, 84, 85, whose outputs 86, 87 and 88 are connected to a microprocessor 89. Differences of the potentials determined at positions 1 to 4 are established in differential amplifiers 83, 84 and 85 and in microprocessor 89 they are converted to partial vectors in a specific orthogonal coordinate system x, y, z. While the invention has been described in some detail above, it is to be understood that this detailed description is by way of example only, and the protection granted is to be limited only by the spirit of the invention and the scope of the following claims.

We claim:

1. A process for processing electrical signals which are tapped by electrodes at a plurality of predetermined times in a physiologically produced electrical field, wherein said field is approximated by a dipole used as a model for said physiologically produced electrical field, comprising the steps of:
   measuring the signals tapped by said electrodes,
   computing a vector from the measured signals which represents the state of said dipole at said predetermined times,
   repeatedly computing said vector at a plurality of said predetermined times; and
   computing a value of a vector triangle derived from a said vector computed at a first said predetermined time and a said vector computed at a second said predetermined time.

2. The process according to claim 1, wherein said step of computing a value of a vector triangle further comprises the step of computing the value and orientation of a time differential vector which is determined starting from said vector computed at said first predetermined time and ending with said vector computed at said second predetermined time.

3. The process according to claim 2, further comprising the steps of:
   computing the difference of the values of said first mentioned time differential vector and a second similar such time differential vector determined based on others of said predetermined times of said plurality of predetermined times.

4. The proces according to claim 1, wherein said predetermined times correspond to periods of time therebetween, wherein said step of computing a value of a vector triangle further comprises the steps of computing a said vector several times with a said period of time, and determining a surface covered by said vectors computed in said period of time.

5. The process according to claim 4, and the steps of repeatedly performing the steps of claim 37 to thereby determine a plurality of said surfaces for others of said periods of time, and comparing each said determined surface with at least one other of said plurality of determined surfaces.

6. The process according to claim 4, wherein said step of determining a surface is performed using at least three of said vectors computed at equally spaced times within a said period of time.

7. The process according to claim 1, further comprising the step of determining a surface which is located between two of said vectors computed at two different ones of said predetermined times.

8. The process according to claim 1, further comprising the step of integrating the value of said vectors computed within a period of time starting with said first predetermined time and ending with said second predetermined time.

9. The process according to claim 8, further comprising the steps of:
computing said vectors within different periods of time corresponding to different pairs of said predetermined times,
integrating the value of said vectors computed within each said different period of time to obtain integrals, and
comparing said integrals obtained from different ones of said periods of time.

10. The process according to claim 1, wherein said predetermined times correspond to periods of time therebetween, wherein said step of computing a value of a vector triangle comprises the step of determining defined values corresponding to different ones of said periods of time, and comparing said defined values corresponding to said different ones of said periods of time with one another.

11. Apparatus for processing electrical signals comprising:
means for tapping signals to be processed from a physiologically produced electrical field,
means for measuring said tapped signals;
means for computing vectors from said measured tapped signals; and
means for computing a value of a vector triangle derived from at least two of said vectors.

12. Apparatus according to claim 11, wherein said means for computing vectors comprises means to compute time differential vectors.

13. The apparatus accordig to claim 11, wherein said means for computing a value of a vector triangle comprises means for determining surfaces generated between at least two of said vectors.

14. The apparatus according to claim 11, wherein said means for computing a value of a vector triangle comprises means for computing the values of said vectors and for integrating said values over a period of time.

15. The apparatus according to claim 11, wherein said means for computing values comprises a computer and memories connected to said computer.

16. A process for processing electrical signals derived from physiological electrical activity of an organism, comprising the steps of:
measuring potential values produced by said physiological electrical activity at predetermined locations on the organism producing said physiological electrical activity and at predetermined different times;
computing vectors from said potential values at said predetermined different times; and
computing value a vector triangle from a said vector computed at a first said predetermined time and a said vector computed at a said second predetermined time.

* * * * *

UNITED STATES PATENT AND TRADEMARK OFFICE
CERTIFICATE OF CORRECTION

PATENT NO. : 4,922,920

DATED : May 8, 1990

INVENTOR(S) : Werner Thie, Johann J. Schmid

It is certified that error appears in the above-identified patent and that said Letters Patent is hereby corrected as shown below:

Column 1, line 58, correct "inventin" to --invention --.

Column 2, line 1, change "FIG. 3" to -- FIG. 5 --.

Column 3, line 6, change "diferences" to -- differences --.

Column 3, line 18, correct "accordig" to -- according --; and correct "twhich" to -- which --.

Column 3, line 55, delete "and".

UNITED STATES PATENT AND TRADEMARK OFFICE
CERTIFICATE OF CORRECTION

PATENT NO. : 4,922,920

DATED : May 8, 1990

INVENTOR(S) : Werner Thie, et al.

It is certified that error appears in the above-identified patent and that said Letters Patent is hereby corrected as shown below:

Claim 4, Column 6, line 60, correct "proces" to -- process --.

Claim 5, Column 6, line 68, correct "37" to -- 4 --.

Claim 13, Column 8, line 13, correct "accordig" to -- according --.

Signed and Sealed this

Twelfth Day of May, 1992

Attest:

DOUGLAS B. COMER

*Attesting Officer*     *Acting Commissioner of Patents and Trademarks*